United States Patent [19]
Davidson et al.

[11] 4,146,603
[45] Mar. 27, 1979

[54] TUMOR SPECIFIC GLYCOPROTEINS AND METHOD FOR DETECTING TUMORIGENIC CANCERS

[75] Inventors: Eugene A. Davidson; Sally D. Bolmer, both of Hummelstown, Pa.

[73] Assignee: Research Corporation, New York, N.Y.

[21] Appl. No.: 770,103

[22] Filed: Feb. 18, 1977

[51] Int. Cl.² ...................... G01N 33/16; A61K 43/00
[52] U.S. Cl. ................................... 424/1; 260/112 R; 424/85; 424/88; 424/12
[58] Field of Search ................ 260/112 R; 424/1, 1.5, 424/12, 85, 88

[56]         References Cited
       U.S. PATENT DOCUMENTS
4,010,251   3/1977   Green .................................. 424/1.5

OTHER PUBLICATIONS

Burger et al., Chemical Abstracts, vol. 72, No. 5, Feb. 2, 1970, p. 153.
Duesberg et al., Chemical Abstracts, vol. 73, No. 17, Oct. 26, 1970, p. 95.
Miroff et al., Nature, vol. 227, No. 5364, Sep. 19, 1970, pp. 1243–1244.
Makita et al., Biochimica et Biophysica Acta, vol. 241, No. 2, Aug. 13, 1971, pp. 403–411.

*Primary Examiner*—Benjamin R. Padgett
*Assistant Examiner*—Christine M. Nucker
*Attorney, Agent, or Firm*—Gerald S. Rosen; Robert J. Sanders, Jr.

[57]           ABSTRACT

A new class of glycoproteins has been found to be produced by human cancer cells and is not produced by normal cells and said glycoprotein is present in the sera of cancer patients. This tumor specific glycoprotein can be characterized by its isoelectric point of from about 4.2 to 4.6 and by the perchloric acid soluble fraction thereof having a sialic acid content of above about 0.065 mg/ml of initial serum sample. The presence of a tumorigenic cancer in a patient can be determined by detecting the presence of the tumor specific glycoprotein in the blood sera of a patient.

17 Claims, 4 Drawing Figures

Fig. 1.

Fig. 2.

TUMOR SPECIFIC GLYCOPROTEINS AND METHOD FOR DETECTING TUMORIGENIC CANCERS

BACKGROUND OF THE INVENTION

Observations in a number of laboratories including my own have demonstrated that animal cells in tissue culture could be made to grow under conditions that would allow them to retain characteristics typical of the tissue from which they were derived. In other words, cartilage cells can be grown in tissue culture and would produce typical cartilage matrix products, pituitary cells would produce pituitary hormones, etc. Among the products which were of interest to our laboratory were a group of complex saccharides normally considered as secretory products of cells in that they are found in the extracellular matrix in which fibrous and cellular elements are resident. This class of compounds has about six representatives with certain common features including aspects of their molecular size and high negative charge. This latter property is most often used in isolation and identification of this particular group.

A study was then carried out wherein direct comparison could be made between a normal cell line and the same cell line after infection with a viral agent which rendered the cell tumorigenic. This work was reported in Proc. Nat. Acad. Sci., USA, Vol. 70, No. 1, pp. 53 - 56, January 1973.

It was found that there was no qualitative difference between the saccharide products but rather a quantitative difference occurred upon viral transformation insofar as the synthesis of one of the characteristic saccharides was concerned. This type of quantitative change is useful for studies in a cell culture system but could never be used for any purpose in animal studies because the particular product involved is normally found in most tissues of the body, is non-antigenic and cannot under any circumstances be considered characteristic of the tumor cell. Nonetheless, the qualitative differences were of interest and were found to be quite general. The conclusion could be drawn that conversion of a cell line by virus transformation involves at least a change in the pattern of complex saccharide synthesis.

As reported in Biochemistry (1974) Vol. 13, p. 1233, my laboratory carried out a similar series of experiments with the B16 mouse melanoma cells and a control population of normal melanocytes derived from the iris of mice. The differences observed between the melanoma cells and the control population were somewhat more striking than those observed for the normal and virus transformed pairs referred to above. These differences can be briefly summarized as follows:

1. There was both a qualitative and a quantitative difference in the production of complex saccharides when the tumor cells were compared with their normal counterparts.
2. In particular, a major product of the normal cells, hyaluronic acid, was not produced at all by the tumorigenic line.
3. A sulfated polysaccharide of unusually high molecular weight was produced by the tumor line but was absent in the normal cells.

With regard to the sulfated polysaccharide, it is important to note that the compound produced differs from normal components of tissue only in its molecular size and not in its molecular architecture. That is, the structure of the saccharide was identical to the structures normally found in tissue materials but the size was somewhat larger. Once again, this is suitable for studies under cell culture conditions but is essentially useless as a diagnostic technique since the compound in question is rapidly metabolized by a variety of cells in host animals. Should such a compound appear in the circulation, it would rapidly be cleared and digested by liver cells, kidney cells, fibroblasts, etc. Therefore, as a diagnostic technique, the presence or production of this saccharide by the tumor cells offered no utility, not only for the reason mentioned above but also because the compound itself is non-antigenic.

In a publication in Cancer Research, 36, 424 - 431, February 1976 I reported the results of a complex saccharide study of human cells which in many respects are similar to those obtained in the mouse. The human melanoma cells produce less hyaluronic acid than the control melanocytes and a high molecular weight sulfated polysaccharide similar to that produced by the mouse cells.

Further studies of the mouse system revealed the presence of an unusual glycoprotein. Accordingly, an effort was made to further understand the nature of the mouse glycoprotein insofar as its properties, structural chemistry and biological function could be defined. Many of the chemical properties of the molecule are described in my paper in *Biochemical and Biophysical Research Communications*, Vol. 70, No. 1, May 1976. The presence of an unusual glycoprotein in the human melanoma cells or its production by them is not reported in this publication although it may be alluded to on page 144 of said paper as unpublished results of my laboratory.

SUMMARY OF THE INVENTION

The present invention resides in the discovery, isolation and identification of a glycoprotein or a class of glycoproteins produced by human cancer cells and that the same kind of glycoprotein is not produced by normal cells. It was further discovered that the unique kind of glycoprotein referred to is present in the sera of patients with cancer and that, therefore, this phenomenon would be of value in the diagnosis and treatment of cancer.

DETAILED DESCRIPTION OF THE INVENTION

A unique kind or class of glycoproteins has been found to be produced by malignant tumor cells which are not produced by healthy or normal cells. This unique kind or class of tumor specific glycoprotein (hereinafter sometimes "TSGP") is present in the tumor, is produced and secreted by the tumor cells and appears in the circulation of the animal host, including humans, more or less at the time that palpable tumor mass can be detected. The TSGP may appear at any earlier stage as well.

The TSGP is generated by the tumor cells regardless of the tumor concerned and appears in the circulatory system of humans suffering from lung, mammary, colon, uterine, and gastric carcinomas, melanomas, and the like. Leukemias and other blood malignancies represent a defect in maturation control resulting in the appearance of abnormal number of cells normally found in developmental pathways. Accordingly, many or most of these blood malignancies may not produce TSGP since the cells themselves are not tumorigenic. Furthermore, leukemias are readily detected by microscopic examination of a blood specimen and do not represent a diagnostic problem.

The specific glycoprotein produced by the host animal having a malignant tumor disease may differ depending on the character and kind of the tumor and the particular host animal involved, but whatever the nature of the tumor, one product will be a member of the kind and class of tumor glycoproteins (TSGP) I have discovered, isolated, and characterized.

It is recognized that the growth characteristics and other properties of tumors of different cellular origin (and from different individuals) will not be the same. However, the glycoprotein type described here appears to be characteristically produced by a very wide variety of tumors. The chemical and physical properties of TSGP have sufficient similarity from one tumor type to another so as to permit standard isolation techniques to be employed throughout.

The following features involving properties, structural chemistry and biological function are characteristic of TSGP and serve to differentiate it from other glycoproteins normally found in the serum:

(a) Solubility in perchloric acid (0.6M) at 0° C. or trichloracetic acid (5%) at 0° C.

(b) Sialic acid or N-acetyl neuraminic acid (hereinafter sometimes "NANA") content of 30% by weight based on the total weight of glucosamine, galactosamine and sialic acid.

(c) Affinity for diethylaminoethyl Sephadex A-25 (Pharmacia Co., Uppsala, Sweden) and elution with pyridine acetate buffer pH 5.2 at approximately 0.4M concentration.

(d) Inclusion on Sephadex G-150 (Pharmacia Co., Uppsala, Sweden) in 0.1M pyridine acetate pH 5.2. Elution at 1.5 × the void volume as calibrated with Blue Dextran.

(e) Affinity for a conjugated wheat germ agglutinin immobilized on a Sepharose carrier, such as a wheat germ Sepharose column in 0.05M sodium or potassium chloride. Other artificial carriers can be used for the wheat germ lectin. Elution from the column specifically with N-acetylglucosamine (0.1M is optimal in water). Other lectins which have an affinity for TSGP but are not as specific include limulus polyphemus (crab) lectin and after removal of sialic acid residues, Ricinus Communis II lectin.

(f) This affinity for the wheat germ agglutinin is lost upon treatment with sialidase (purified by affinity chromatography so as to be free of protease) from any of several sources. An important criterion in this analysis is that complete removal of the sialic acid from TSGP is not required to destroy the affinity for wheat germ agglutinin.

(g) The sialic acid in TSGP is linked to galactose and may also be linked to N-acetyl galactosamine.

(h) Electrophoresis of TSGP in 6% polyacrylamide gels in the presence of sodium dodecyl sulfate (0.1%) and staining of the gel for protein and carbohydrate reveals that TSGP has a molecular weight of from about 50,000 to 70,000, and probably about 60,000. There is an uncertainty in this figure since glycoproteins generally give anomalous molecular weight values by this technique. However, the glycoprotein will enter and migrate in a 6% crosslinked gel. Following pronase digestion the molecular weight is reduced to the range of about ten to fifteen thousand (10,000 to 15,000). This represents a protease resistant core suggesting that the sialic acid residues and the saccharide substituents are clustered on the polypeptide backbone.

(i) Isoelectric focusing in gels or solution clearly separates TSGP from any contaminating serum components (such as α-1 acid glycoprotein). TSGP has an isoelectric point of about 4.2 to 4.6 and may exhibit several closely spaced bands due to slight differences in sialic acid content.

(j) TSGP also contains neutral hexose, mainly galactose; no glucose is present. Detection is possible by analysis for neutral sugar (as by the method of Dubois et al, Anal. Chem., 28, 350 (1966).

(k) TSGP can be shown to be a product of human tumor cells grown in monolayer culture in vitro.

(l) The main carbohydrate portion of TSGP which contains the bulk of the sialic acid is linked to the polypeptide moiety via an O-glycosidic bond from a single N-acetylgalactosaminyl residue to the hydroxyl group of serine or threonine (a partial sequence may be galactosyl-N-acetyl galactosamine substituted by sialic acid residues in the three and six positions, respectively).

(m) This entire saccharide chain can be cleaved from the polypeptide by treatment with 0.01N sodium hydroxide for 16 hours at 20° C. The resulting saccharide chain may be separated on a G25 Sephadex column (1.2 × 60 cm) and elutes at 1.15 × the void volume as calibrated with Blue Dextran.

(n) The amino acid composition of TSGP fraction after chromatography on DEAE-Sephadex A=25 shows glutamic acid, proline, aspartic acid, threonine and leucine as the major amino acids.

Summarizing the foregoing, the distinguishing characteristics of tumor specific glycoproteins isolatable from the blood sera of cancer infected humans are that it is soluble in 0.6M perchloric acid, the high sialic acid content of the perchloric acid soluble fraction, i.e. above about 0.065 mg of sialic acid per ml of initial serum sample and preferably above about 0.80 mg/ml, a pronase resistant core containing the bulk of the carbohydrate, affinity for wheat germ agglutin dependent on sialic acid, particular electrophoretic and chromatographic mobility, a molecular weight in the range of from about 50,000 to 70,000, and an isoelectric point of from about 4.2 to 4.6. The particular characterizing properties of tumor specific glycoprotein found useful for diagnostic purposes to distinguish it from other glycoproteins in normal patient sera is that the TSGP has an isoelectric point of from about 4.2 to 4.6 and the perchloric acid soluble fraction has a sialic content above about 0.065 mg per ml of initial serum sample.

For ease of understanding and description some of the products used herein are designated by their trade designations. Detailed descriptions of these products are unnecessary because they are readily recognized by those skilled in the art and further descriptive material is available from the manufacturers of the products. Briefly, however, "Sephadex" products are made and sold by Pharmacia Fine Chemicals A.B. of Uppsula Sweden, and they are cross-linked dextrans with differing porosity or substituents. "Sepharose" is a bead-formed agarose gel. "DEAE Sephadex A25 or A50" is prepared from Sephadex G25 or G50 by chemical substitution with diethyl aminoethyl groups. They are weakly basic anion exchangers. They have bead diameters of 40-120 microns and swell to bed volume of 8 ml per gram of dry gel for Sephadex G-25 and 15-25 ml per gram of dry gel for Sephadex G-50. Sephadex G150 has a bead size of 40-120 microns, a fractionation range of 5 - 150,000 molecular weight and a bed volume of 20 - 30 ml per gram dry gel. Sepharose 4B has an agarose concentration of 4% and a wet bead diameter of 40 - 190 microns.

It is noted that TSGP can be differentiated from carcinoembryonic antigen such as described in U.S. Pat. No. 3,663,684 by, among other factors, the inclusion of TSGP on Sephadex G150 (property (d) above), the affinity of TSGP for a conjugated wheat germ agglutinin immobilized on a Sepharose carrier (property (e), above), and molecular weight (property (h), above), none of which properties are possessed by carcinoembryonic antigen.

My discovery that this unique kind or class of glycoproteins is present in tumors, is produced and secreted by the tumor cells and appears in the circulation of the animal including human hosts and my identification and characterization of the TSGP has led me to the following useful objects:

I. Early diagnosis of individuals with any kind of malignant tumor disease.

II. Detection or analysis of the unique TSGP in a sample of human blood through radioimmune or other assay techniques as a means for diagnosis or treatment of cancer.

III. Individualized therapy by isolation of quantities of the TSGP from patients having advanced cancer through plasmapheresis or otherwise and utilizing this material to permit direct antibody production in a host animal or the patient and utilizing this antibody in directed immunotherapy. Coupling of this antibody with agents toxic to cancer cells would permit introduction of lethal agents into cancer cells as targets.

IV. Utilization of the TSGP isolated from a cancer patient to produce antibodies which can attack the surface of the tumor cell permitting antibody mediated lysis by the normal immune system of the host or produce alterations in the surface of the tumor cells to permit conventional therapeutic agents to be more highly effective.

V. Determination of the level of the glycoprotein in a patient's serum and utilization of this information as a direct index of a therapeutic regimen.

I. EARLY DIAGNOSIS OF INDIVIDUALS WITH ANY KIND OF MALIGNANT DISEASE:

I have found that the presence of TSGP in human sera can serve to provide a direct indication of the presence of a malignant tumor (other than blood malignancies) in the patient sampled, and have developed a simple yet accurate method of detecting the presence or absence of TSGP in human sera. Thus, I have developed a generalized diagnostic screen which is non-invasive and non-destructive and which can be applied as part of a routine physical examination of patients in the age group which may be at a risk, i.e. women over 40, men in certain occupations, etc. On the basis of a single blood sample, the technique can be utilized as part of a routine health examination for all individuals of any age.

The original analytical screen for TSGP was based on the following properties of TSGP:

1. The glycoprotein has a very high negative charge.
2. The negative charge was due mainly, if not exclusively, to the presence of N-acetyl-neuraminic acid.
3. The N-acetyl-neuraminic acid was present on saccharadicchains which tended to cluster and provide a core structure resistant to proteolysis.
4. This highly acidic structure was soluble in an appropriate concentration of perchloric acid or trichloroacetic acid or other suitable solvents.
5. The glycoprotein has affinity for wheat germ agglutinin immobilized on Sepharose.
6. The glycoprotein due to its high negative charge can be fractionated on a variety of anionic exchange supports including diethylaminoethyl cellulose, diethylaminoethyl sephadex, ecteola cellulose, and strong and weak anion exchange resins such as Dowex 1 or Dowex 2.
7. The high carbohydrate content of the glycoprotein and its charge permits identification by polyacrylamide or other gel electrophoresis methods and staining either by conventional protein stains or by stains for the carbohydrate moiety utilizing periodic acid-Schiff or similar reagents.

Briefly then, the diagnostic screen is based on the generalized and common structural features of the glycoprotein, that is, the high sialic acid content, pronase resistant core, affinity for wheat agglutin and characteristic electrophoretic and chromatographic mobility.

The general method employed for determining the presence of TSGP in human blood serum comprises obtaining a serum sample from a human patient; treating the serum sample with a TSGP solvent such as perchloric acid, trichloroacetic acid or other suitable solvent material; removing the precipitate formed by any suitable technique for solid-liquid separation, such as decantation, filtration, or centrifugation; neutralizing the soluble fraction with an alkaline material, such as potassium hydroxide, analyzing the soluble portion for N-acetyl-neuraminic acid and protein content; and comparing the levels of N-acetyl neuraminic acid and protein content obtained against baseline parameters established for normal and cancer sera.

Analysis for NANA may be by any of the conventional procedures known in the art including the periodate-resorcinol, thiobarbituric acid or direct Ehrlich methods. [See G. W. Jourdian et al, J. Biol. Chem., 246, 431 (1971); L. Warren, J. Biol. Chem. 234, 1971 (1959); and I. Werner et al, Acta Med. Soc. Upsal. 57, 230 (1952)].

The protein determinations may be made, for example, by a modified Coomasie blue G procedure or by the Lowry procedure or by measuring absorbancy at 280 nm. [See O. H. Lowry et al, J. Biol. Chem. 193, 265 (1951) and M. M. Bradford, Anal. Biochem. 72, 248 (1976)].

Based on the combined data from 370 human samples, the following parameters for determining the presence of malignant tumors in humans have been assigned (based on analysis of the perchloric acid soluble fraction related to volume of initial serum sample):

1. Sialic acid (NANA) above about 0.065 mg/ml indicates possible tumor and a sialic acid content above about 0.080 mg/ml indicates a probable tumor.
2. Protein content above about 0.35 mg/ml indicates a possible tumor and a protein content above about 0.4 mg/ml indicates the probable presence of a tumor.

An initial study was carried out with 59 samples using the periodate-resorcinol and direct Ehrlich methods for N-acetyl-neuraminic acid levels and the Lowry procedure for protein levels. It was found that between 30 cancer patients and 29 normal controls there was complete discrimination in the levels of sialic acid. That is, the highest normal level was still lower than the lowest level found in a patient with diagnosed malignant disease. A number of malignancies of different types, lung, mammary, colon, lymphoma, and melanoma patients, were covered in this initial screen, suggesting that the production of a perchloric acid soluble glycoprotein was a general characteristic of a a variety of tumors. The statistical analysis of these data showed that the probability that these results might occur by chance is less than 1 in 1,000.

Utilizing the levels obtained in the above study as parametric criteria, a much larger study was conducted of some 311 patients with both malignant disease and with a variety of non-malignant conditions as well as a number of normal control individuals. Based simply on protein and sialic acid levels (N-acetyl-neuraminic acid), better than 95% discrimination was obtained between normal and non-malignant diseased individuals as opposed to patients with tumor. Furthermore, there was no significant difference between normal and non-malignant diseased individuals or between males and females. A number of other statistical tests have been conducted with the data derived from this group of samples. Suffice to say, the probability of the distinction between the cancer and other group occurring purely by chance is less than one in one thousand. There is also a clear correlation with the progress of disease. Thus, individuals with disseminated, widespread metastatic disease have higher levels of circulating TSGP than do those with localized disease; individuals in remission or following surgery and/or chemotherapy or radiation treatment tend to have lower levels of circulating glycoprotein.

These results were sufficiently striking to warrant a variety of further studies. My first concern was for the few false positives that showed up in this group. It should be noted that several of these were from asthmatic patients and may indeed be related to some factor associated with that disease.

Accordingly, I conducted a further study on the false positives, normals and several patients with diagnosed cancer to ascertain if the qualitative differences established in the cell culture system could be duplicated in the serum sample. Rather than simply looking at the levels of N-acetyl-neuraminic acid in the perchloric acid soluble fraction, the perchloric acid soluble material was examined by gel electrophoresis (as specifically described hereinafter in Example 2) for the presence of the characteristic tumor glycoprotein (TSGP). The tumor specific glycoprotein has an isoelectric point of from about 4.2 to 4.6, and a molecular weight of from about 50,000 to 70,000 generally about 60,000.

When this second screen is performed, the number of false positives was reduced to 0; only patients with diagnosed tumor showed a characteristic glycoprotein band on gel electrophoresis. Thus, although a few individuals with malignancies (particularly leukemias) had levels of N-acetyl-neuraminic acid which were not in the abnormal group, there were no normal or non-malignant diseased normals in the positive group after the second screen. Furthermore, the presence of the characteristic glycoprotein could be demonstrated in those individuals with malignant disease but with lower levels of N-acetyl-neuraminic acid.

In summary, the screen I have developed has demonstrated the following:

1. There is an unusually high degree of reliability in predicting tumor incidence and disease state based simply on measurement of N-acetyl-neuraminic acid and protein levels in the perchloric acid soluble fraction of serum.

2. A very small number of false positives can be completely eliminated by a second screen involving gel electrophoresis and examination of the gels for the presence of the characteristic tumor specific glycoprotein.

3. The predictability value of this technique is at least as good or better than any currently or previously described including carcinoembryonic antigen such as described in U.S. Pat. No. 3,663,684.

4. TSGP, while it might not be identical for all tumors or indeed even for all lung carcinomas, for example, nonetheless, has sufficient identity in structural characteristics to afford a generalized diagnostic screen. It is important to recognize that two different individuals with the same anatomical diagnosis may nonetheless have tumors with different characteristics insofar as the rate of metastasis, rate of growth and characteristic products are concerned. The possibility remains that every tumor represents a different biological entity and a different disease and that no two are identical insofar as characteristic cell products are concerned. Thus, the need for a generalized identification technique and generalized therapeutic strategy is paramount before any reasonable progress can be expected with respect to either early identification or therapeutic regimens of wide applicability. The fact that a tumor specific glycoprotein is present in human sera as a product of tumor growth thus provides such a general diagnostic tool.

The following examples are given to illustrate embodiments of the invention as it has previously been described and as it is now preferred to practice it. It will be understood that these examples are illustrative, and the invention is not to be considered as restricted thereto except as indicated in the appended claims.

EXAMPLE 1

Purification and Isolation of Tumor Specific Glycoprotein

Serum samples as obtained from patients with diagnosed solid tumors (lung, gastric and mammary carcinoma and melanoma have been used and each showed similar chromatographic and electrophoretic mobility) are treated as follows:

70 microliters of 60% perchloric acid is added per ml of serum and the solution mixed. To this solution is added 0.93 ml of 0.6M perchloric acid per ml of serum. The solution is mixed well and allowed to stand for one hour (45–90 minutes is satisfactory) at 0° C. The mixture is then centrifuged at 8,000 xg for 10 minutes (6–12 minutes) and the supernatant fluid recovered by decantation from the precipitate.

The resulting supernatant solution is adjusted to pH 6–7 with 1.2M potassium hydroxide and allowed to stand for 10 minutes at 0° C. The potassium perchlorate is removed by centrifugation as above (filtration is satisfactory) and the supernatant fluid dialyzed against $10^{-3}$M pyridine acetate pH 5.2 for 24 hours (16–36 hours is satisfactory).

A column of DEAE-Sephadex A-25 (1.5 × 40 cm) is prepared according to the directions of the manufacturer and equilibrated with 0.1M pyridine acetate pH 5.2.

The dialyzed perchloric acid supernatant sample is concentrated about 10-fold by lyophilization (preferred) or ultrafiltration. An aliquot containing up to 5 mg of sialic acid and up to 30 mg protein is applied to the column and the column is then eluted with a linear gradient from 0.01M to 1.0M pyridine acetate pH 5.2 (total gradient volume is 600 ml). Fractions are collected at a flow rate of 30 ml per hour (5–6 ml fractions). The fractions are analyzed for protein and sialic acid content by the Lowry et al and periodate-resorcinol methods, respectively. The major sialic acid positive fraction eluting at a gradient concentration of about 0.4M is combined, dialyzed against distilled water at 0° C. for 24 hours and concentrated by lyophilization. This fraction contains the tumor specific glycoprotein and may contain some α-1 acid glycoprotein, a normal serum component.

Further purification of the tumor specific glycoprotein may be achieved by isoelectric focusing or chromatography on DEAE-Sephadex A-50.

The sialic acid containing fraction obtained from the above chromatography is applied to a 1.2 × 50 cm column of DEAE-Sephadex A-50 and the column eluted with a linear pyridine-acetate gradient (0.01M-0.5M, pH 5.2, 400 ml). Two sialic acid positive fractions are obtained eluting at gradient concentrations of 0.42 and 0.46M respectively. The second fraction contains the tumor glycoprotein and is substantially free of other contaminants. This fraction is desalted by dialysis against distilled $H_2O$ for 24 hours at 0° C. and concentrated by lyophilization.

Alternatively, the tumor specific glycoprotein fraction obtained from the DEAE-Sephadex A-25 column is subjected to gel isoelectric focusing in a pH 3.5–7.0 ampholine gradient using an LKB-multiphor apparatus from LBK Instruments, Inc. Contaiminating acid glycoproteins have isoelectric points of 3.5–3.8 and are clearly separated from the tumor specific glycoprotein which has an isoelectric point of 4.4 (4.2–4.6). The same principle can be used for preparative work using a 110 ml Ampholine column (LKB) and the same pH gradient described above. The region between pH 4.2 and 4.6 is collected, dialyzed against distilled water and concentrated by lyophilization. The product may be dissolved in 0.01M sodium or potassium chloride containing 0.005M phosphate buffer pH 6.5.

Final purification as well as a check for contamination may be achieved by affinity chromatography of the glycoprotein on a wheat germ agglutinin-Sepharose column.

The glycoprotein solution (in sodium chloride-phosphate 0.01M–0.005M, pH 6.5) is applied to a 1 × 10 cm column of Sepharose 4B conjugated with wheat germ agglutinin equilibrated with the same solution. The column is washed with 3–5 volumes of the equilibrating buffer (none of the tumor glycoprotein should be eluted from the column). The tumor glycoprotein can be eluted in a sharp, symmetrical peak with 0.1M N-acetylglucosamine. The sugar is removed by dialysis against distilled water and the glycoprotein concentrated by lyophilization.

EXAMPLE 2

Polyacrylamide Gel Electrophoresis

Solution A is prepared by mixing 0.24 g of acrylamide (obtained from Eastman Organic DPI and recrystallized twice from acetone) with 0.73 g of N,N'-methylenebisacrylamide and 100 ml of water. Solution B is prepared by dissolving 150 mg of potassium or ammonium persulfate in 100 ml of water. Solution C contains 7.7g $NaH_2PO_4.H_2O$, 38.6 g $Na_2HPO_4.7H_2O$, 4 g sodium dodecyl sulfate and 1.15 ml of N,N,N', N'-tetramethylethylene diamine (Eastman DPI) per liter. The gel was prepared by mixing one part of Solution A with two parts of Solution B and one part of Solution C. The mixture is immediately added to a 5 × 75 mm gel tube of a height of 55 mm. The gel is overlayed with 10 mm of $H_2O$ and the prepared tube is permitted to stand for 1 hour at 25° C. The tube is inserted into the reservoir. A sample, 10–25 μl, containing 5 to 20 μg of glycoprotein, is layered on top of the gel surface and the electrophoresis run at 70V for 2 hours. The gel is removed and fixed with 10% trichloroacetic acid for 3 minutes and then stained with 0.3% Coomassie Brilliant Blue R in 10% acetic acid - 45% methanol-45% $H_2O$ for two hours at 40° C. The material is destained with 7% acetic acid - 30% methanol- 63% $H_2O$ five times for two hours at 40° C. (or longer at 25° C.). The glycoprotein staining procedure used was in accordance with that described by Zacharius et al, Anal. Biochem., 30, 148 (1969).

EXAMPLE 3

Determination of Sialic Acid (NANA) And Protein Levels In Perchloric Acid Soluble Glycoprotein Fractions Of Cancer And Normal Patients Serum samples were collected from 30 cancer patientsd including those having mammary, lung, colon, lymphoma, and melanoma cancers and 29 normal control individuals. The serum sample of each patient and control is admixed with perchloric acid, the soluble fraction recovered after removal of the precipitate, and the soluble fraction neutralized, all as described in Example 1 above. The neutralized perchloric acid soluble fraction is analyzed for protein by the Lowry et al method and for sialic acid by the Direct Ehrlich procedure. The data obtained is summarized in FIGS. 1–4.

Figure 1:
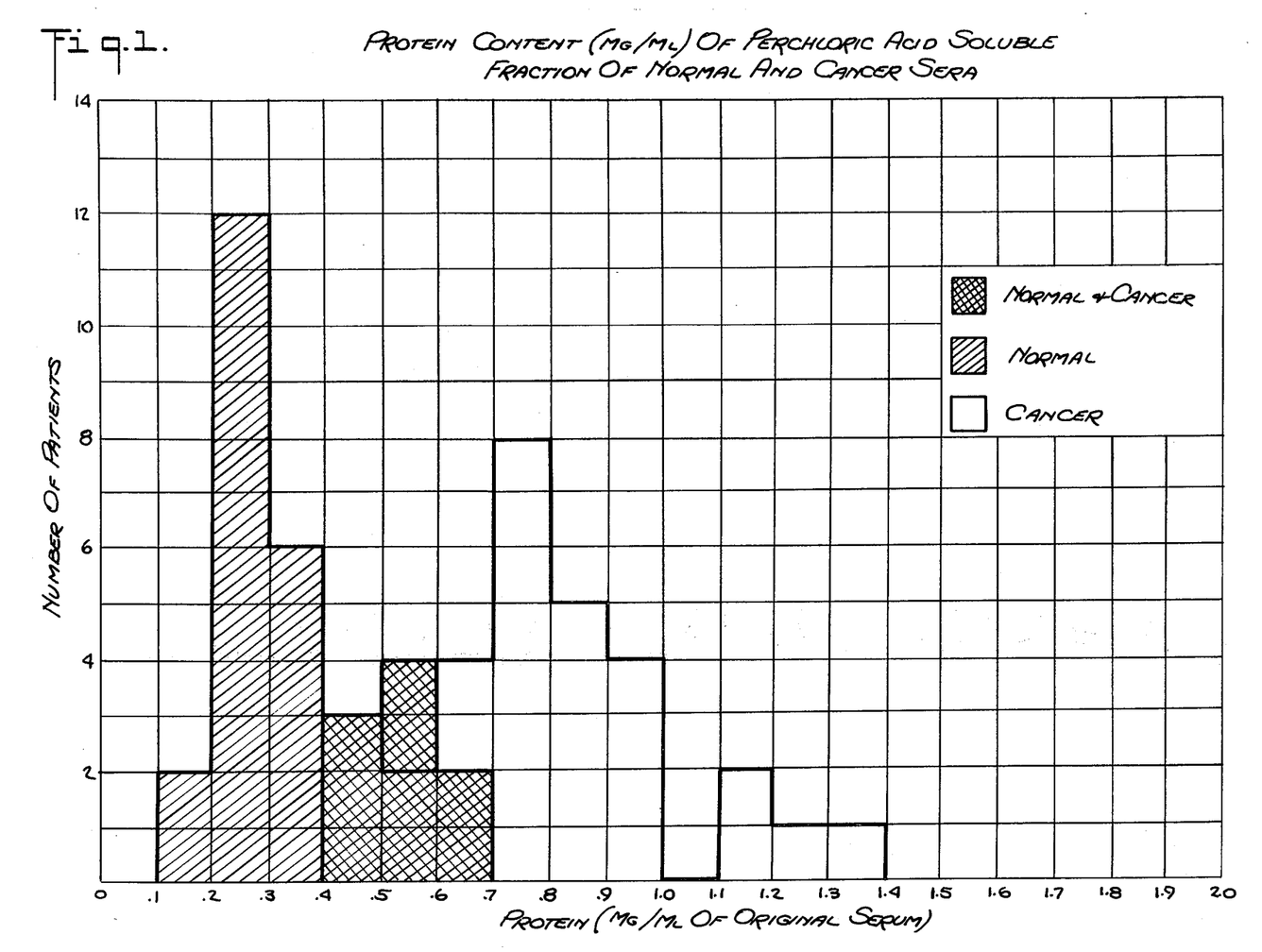

FIG. 1 shows the amount of protein found (mg/ml) in the perchloric acid soluble fraction of both the normal and cancer samples. The average protein for normals in individuals is 0.35 mg/ml and the average protein for cancer patients is 0.79 mg/ml. The difference is significant at a value of less than 0.001 (less than 1 chance in 1,000 that this can occur by chance).

Figure 2:
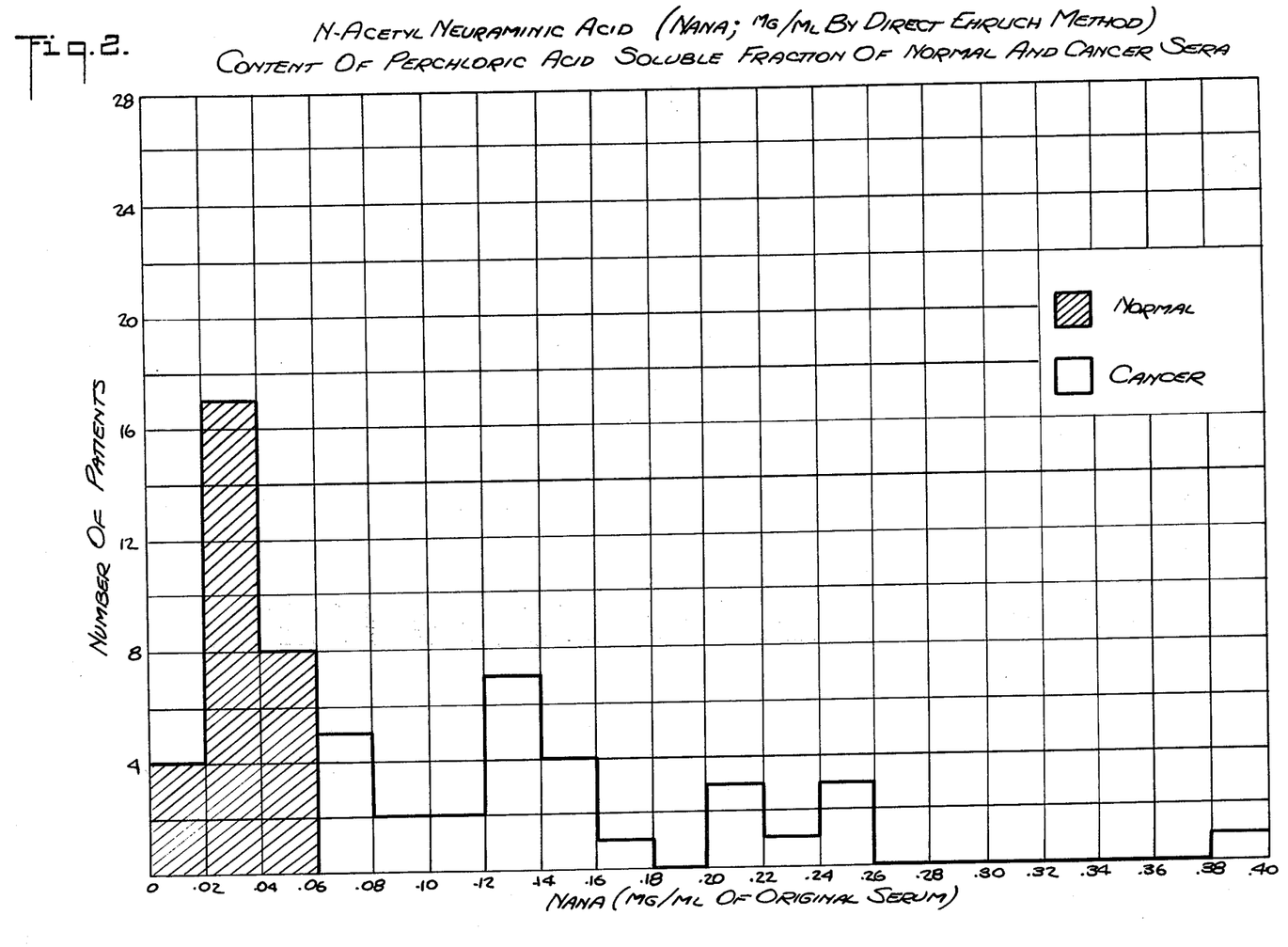

FIG. 2 shows the amount (mg/ml) of sialic acid (NANA) found in the perchloric acid soluble fraction of the samples of both the normal individuals and cancer patients. The average sialic acid for normals was 0.034 and the average for cancer patients was 0.162 ($\alpha << 0.001$).

Figure 3:
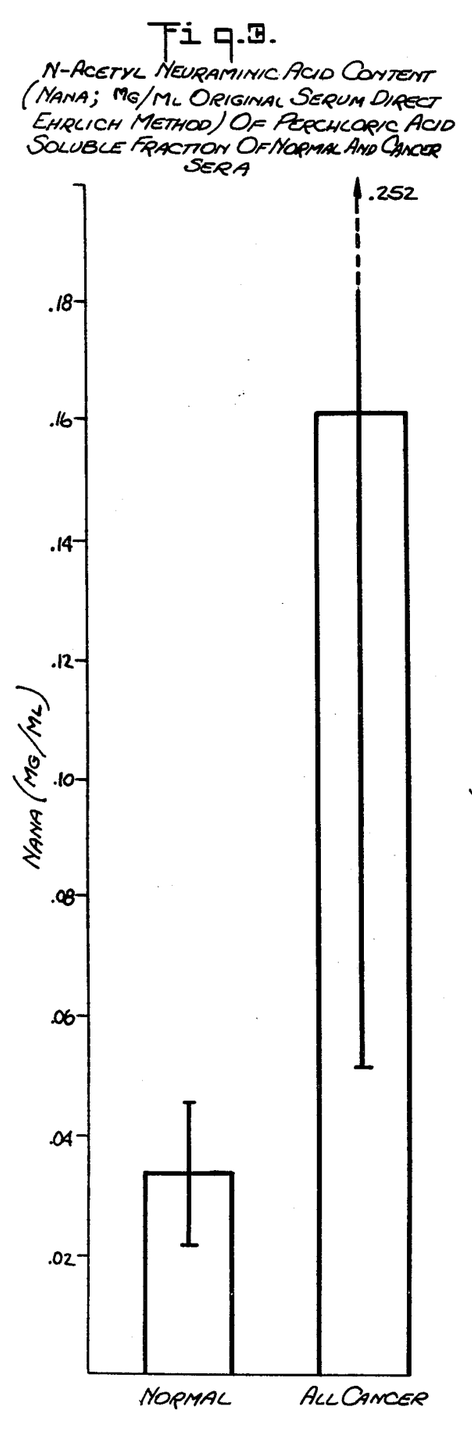

FIG. 3 is a replot of the data in FIG. 2 showing the range of sialic acid content in both normal and cancer individuals and a comparison between them.

Figure 4:
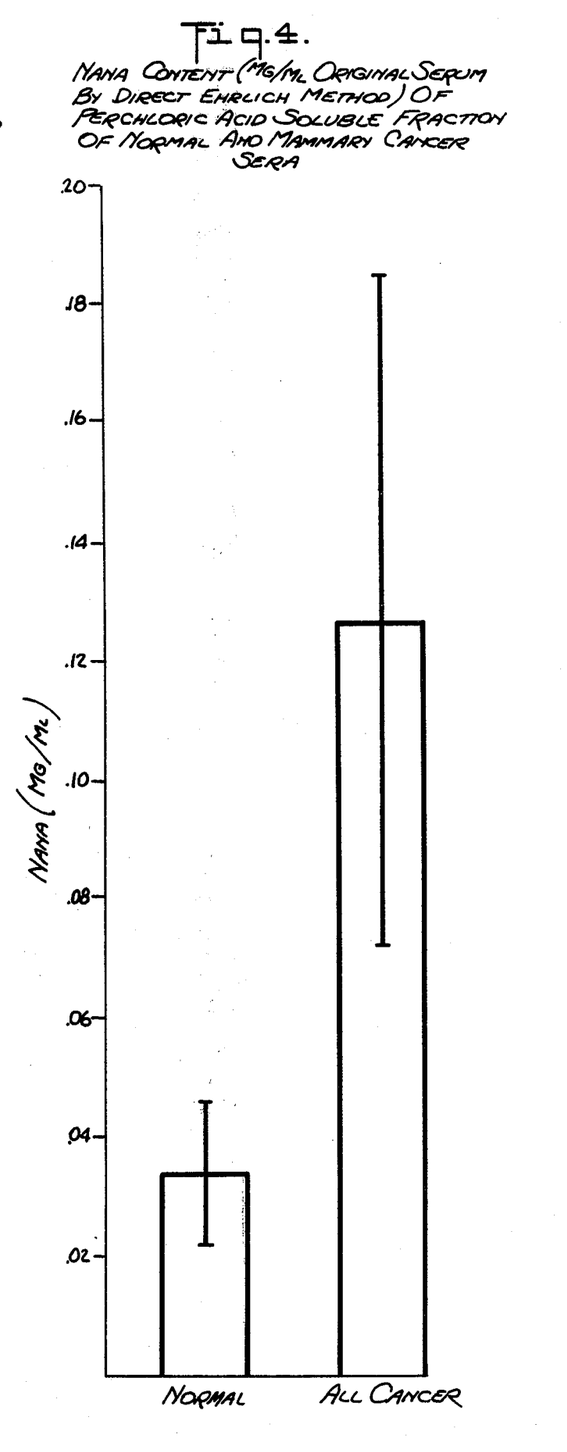

FIG. 4 shows the range of sialic acid content in normal individuals and individuals with mammary cancer.

EXAMPLE 4

Determination of Sialic Acid (NANA) And Protein Levels In Perchloric Acid Soluble Glycoprotein Fractions Of Cancer and Normal Patients A second series of 311 individuals were studied using a blind, controlled coding. The group of individuals included those having solid and blood tumors (leukemia). The cancer patients in the group included the following cancer types: lymphoma, breast, bowel, melanoma, sarcoma, testicular, rhabdomyosarcoma, lung, kidney and cervical. A number of the individuals examined suffered from a wide variety of non-malignant diseases or conditions including: pregnancy, ulcers, asthma, infectious disease, trauma, cardiac. Other individuals were healthy normal. The serum specimens of all 311 individuals were treated and analyzed as described in Example 3.

Based on the data obtained in Example 3, above, ranges were established for normal levels of sialic acid and protein in the perchloric acid soluble fraction. The levels were established as for "possible tumor": sialic acid above 0.065 mg/ml, and protein above 0.35 mg/ml. Samples falling above this range were diagnosed as possible tumor. Samples having a level of sialic acid above 0.080 mg/ml and a protein level above 0.4 mg/ml were diagnosed as highly probable tumor.

The results of the diagnoses based on sialic acid and protein levels were as follows: percent correctly diagnosed as having malignant disease: 83%, with a 95% accuracy based on the highly probable levels noted above. It should be noted that a number of the cancerous patients were on chemotherapy or were receiving radiation treatments. The total number in this group was too small to ascertain if either of these had a direct effect on serum NANA levels or the presence of the TSGP. The percent "false" positives was 12%.

The false positive group was further examined by subjecting the patients' sera sample to polyacrylamide gel electrophoresis as described in Example 2, above. The tumor specific glycoprotein was not found in any of the samples studied including the asthmatic non-malignant disease patients.

II. RADIO IMMUNE ASSAY FOR DETECTING TUMOR SPECIFIC GLYCOPROTEIN

Utilizing adequate amounts of material obtained from human patients with wide-spread disease and high glycoprotein levels, the tumor specific glycoprotein can be purified by a combination of techniques including affinity chromatography, ion exchange chromatography, isoelectric focusing and others and an antibody developed to this glycoprotein utilizing any number of immunologic techniques. Initially, rabbits, guinea pigs or hamsters are used as the host for development of the first level antibody. While the foregoing is suitable, it may be desirable or preferable to modify the tumor specific glycoprotein by modification of the sialic acid as by reaction with amines or hydrazides after periodate treatment or by partial removal or hydrolysis of the sialic acid (utilizing sialidase from any number of sources — *vibrio cholera, hemophilus influenzae, clostridium species, diploccocus pneumoniae* or others) to further uncover carbohydrate groupings which may be more immunologically reactive.

After obtaining the antibody to the tumor specific glycoprotein in the appropriate host animal, antibodies to this are prepared by injection of the globulin fraction from the host into a goat. Thus, for example, goat anti-rabbit antibody is produced which is radiolabelled with radioiodine or by other suitable techniques. Alternatively, the TGSP can be radiolabelled with $^{125}I$ or $^{3}H$ according to R. O. Hynes, *Proc. Natl. Acad. Sci.*, USA 70, 3170 (1973) or Liao et al, *J. Biol. Chem.* 248, 8247 (1973). A radioimmune assay capable of detecting lower levels of the glycoprotein by highly specific immunologic techniques can thus be obtained. This provides a level of sensitivity which may be 100 to 10,000 times greater than that obtained by the purely chemical procedures thus described above.

Since it can be established that the tumor glycoprotein is produced even by very few tumor cells when grown in culture, it is reasonable to believe that very small foci of tumor will produce and secrete this glycoprotein which then appears in the circulation of the individual. A highly sensitive detection method, such as the radioimmune assay, has the capacity for identifying the presence of this component before the appearance of any manifest symptoms such as pain, discomfort, tissue lumps, etc. Thus, a positive test by this technique would suggest to the examining physician the need for further and more careful diagnostic screening of the patient to ascertain the nature, type and location of the tumor. This will permit early treatment before tumor growth and metastasis occurred. There is little question that early diagnosis and treatment of cancer is still the most effective means of combating the high mortality rate associated with this disease.

EXAMPLE 5

Antibody Production

The purified tumor specific glycoprotein such as that obtained in Example 1 (0.5 mg in 1 ml of 0.15M NaCl) is admixed with an appropriate agent (Freund's adjuvant) and injected into a suitable animal. The injection can be subcutaneous, intramuscular (larger volumes, 3-4X) in the foot pad or some combination; rabbits, guinea pigs, horses or goats may be so treated. In rabbits, the injection would be repeated weekly for a period of 6 weeks, following which blood may be collected from the rabbit and serum prepared. This serum is unabsorbed TSGP (tumor specific glycoprotein) serum. This may then be absorbed with normal serum and any precipitate separated. The supernatant will contain the antibody with specificity for the TGSP.

EXAMPLE 6

Modification of Functional Groups On TSGP

Selective structural modification of the tumor specific glycoprotein to enhance its immunological properties and provide a mechanism for attachment of specific functional groups. The TSGP sample is prepared at a concentration of 1 mg/ml in 0.1M pH 5.0 acetate (sodium or potassium) buffer. This solution is mixed with an equal volume of a solution containing 2-4 micromoles of sodium metaperiodate in the same buffer. The mixture is allowed to stand at 0° C. for 30 minutes and the residual periodate destroyed by addition of 5 $\mu$moles of sodium arsenite. The modified TSGP may now be reacted with any of several amines or hydrazides as described in K. Itaya et al, *Biochem. Biophys. Res. Comm.* 64, 1028 (1975). This procedure specifically alters the sialic acid groupings on the molecule and permits their conversion to a more immunologically responsive grouping. The derivatized TSGP may then be used for antibody production as described above.

EXAMPLE 7

Hydrolysis of Sialic Acid Groupings of TSGP

Commercial sialidase from *vibrio cholerae* or *clostridium perfingens* is purified by affinity chromatography [see P. Cuatrecasas, *Biochem. Biophys. Res. Comm.*, 38, 947 (1970)]. The TSGP is prepared at a concentration of 1-2 mg/ml in pH 5.0 acetate (potassium) buffer containing 2mM calcium acetate. This solution is mixed with a solution containing 50 milliunits of purified sialidase in the same buffer. The mixture is incubated for 18 hours (12–24 hours) at 37° C. The modified TSGP is separated from the released sialic acid by chromatography on a cross-linked dextran gel 1 × 60 cm column in pH 5.0 acetate buffer (e.g. Sephadex G-50 which has a molecular weight exclusion limit of about 50,000 and a particle size of 30–100 microns). The modified TSGP appears in the void volume (first protein peak) and after dialysis against distilled water for 24 hours and concentration by lyophilization the material may be used directly for antibody production as described above.

II. RADIOIMMUNOASSAY:

Radioimmunoassay techniques of several kinds may be employed to detect TSGP in the serum. Typically, direct competition, prior binding and double antibody binding methods will be described.

The direct competition method utilizes TSGP, radiolabelled TSGP ($^3$H or $^{125}$I material may be used) and TSGP antibody (prepared in rabbits, for example). A standard titration curve is developed by addition of a series of known concentrations of TSGP to a set of test tubes which contain aliquots of the perchloric acid supernatant of normal serum equivalent to the volume of serum to be analyzed (typically 1–5 ml). This mixture is prepared in 0.1M sodium potassium phosphate buffer pH 7.2. An aliquot of TSGP-antiserum is now added (to each tube) sufficient to react with all of the TSGP present in the tube with the highest concentration. This mixture is allowed to stand at 4° C. for 16 hours following which a fixed amount ($5 \times 10^3 - 2 \times 10^4$ counts per minute) of radiolabelled TSGP is added. After incubation for 2 hours at 37° C., the antibody and antigen-antibody complex are precipitated by addition of a suitable agent such as saturated ammonium sulfate, or goat anti-rabbit antiserum (see below). Thus, free TSGP remains soluble and the amount of radiolabelled TSGP in the soluble fraction may be determined by counting in a liquid scintillation spectrometer ($^3$H) or a gamma scintillation counter ($^{125}$I). These data permit the construction of a standard titration curve from which the concentration of TSGP in an unknown serum sample carried through the above procedure may be deduced.

The prior binding RIA (radioimmune assay) procedure depends on coupling of the TSGP antibody to an insoluble matrix support such as Sepharose 4B producing a reusable bound, particulate antibody (AB Sepharose). This preparation is then incubated with known amounts of TSGP and radiolabelled TSGP as described above to prepare a standard titration curve. The TSGP antibody-Sepharose complex can be recovered by filtration and washed with 0.15M NaCl to remove mechanically trapped material. Elution of the bound TSGP may be accomplished ($10^{-3}$M KOH or suitable buffer) without destruction of the AB-Sepharose (thus permitting its reutilization). The radioactivity in the eluted TSGP fraction is measured and the data used to prepare a standard titration curve as above. In carrying out the RIA assay the test sample to be analyzed for TSGP is then incubated with the labelled antigen and the antibody and the radioactivity of the eluted fraction is measured as described above.

Instead of using Sepharose as a carrier, the antibody may be bound to plastic surfaces such as discs or test tubes in the manner described by Catt, Science, 158, (1967), p. 1570, or U.S. Pat. No. 3,646,346, and the test procedures described therein may be utilized.

The double antibody technique requires that antibody to the TSGP-antibody be prepared (e.g. goat anti-rabbit). This can then be used to precipitate the TSGP-TSGP antibody complex using levels of TSGP antibody much lower than those described above. Standard curves are prepared in a similar fashion (direct competition) except that one tenth to one hundredth the amounts of TSGP antibody are employed. The precipitation of the TSGP-antibody complex is carried out by addition of the second (goat) antibody and incubation at 4° C. for two hours. The precipitate is recovered by centrifugation, washed with saline and assayed for radioactivity.

Instead of radiolabelling TSGP the TSGP antibody may be so labelled and the amount of TSGP present in a test sample determined by incubating and measuring the radioactivity of bound and unbound fractions. The labelled antibody can be coated on a solid surface or on suitable carrier particles and utilized as a reagent to be contacted with test samples containing TSGP.

The above procedures can be used to detect via RIA very low levels of the TSGP with high specificity. Accordingly, early identification of the presence of malignant foci may be possible based on routine RIA analysis of serum samples. The presence of TSGP should serve as a signal to the likelihood of developing tumor and the necessity for further diagnostic studies.

III. INDIVIDUALIZED THERAPY BY ISOLATION OF TSGP AND PRODUCTION OF ANTIBODIES:

The technique of plasmapheresis allows one to obtain up to 500 ml of serum from a single individual. Thus, sufficient quantities of TSGP should be isolatable from a single patient to permit the production of antibodies. These antibodies will be directed against the TSGP and the surface of the tumor cells. (We have demonstrated that TSGP is detectable on the surface of tumor cells grown in culture in the laboratory.) Interaction of this antibody with the tumor cells may result in the sensitization of the cells to lysis by the normal immune systems of the host. Thus, complement or cell mediated lysis of target cells is frequently enhanced in the presence of agents which interact with the cell surface. Avoidance of random precipitation of antibody with circulating or soluble TSGP may be achieved by the use of Fab monovalent antibody fragments.

IV. UTILIZATION OF TSGP FOR FACILITATING CHEMOTHERAPY:

Given that antibodies can be produced from TSGP isolated from a single individual and that such antibody molecules will be directed against the surface of the tumor cells, it should be possible to utilize this vehicle as a specific carrying agent for functional chemical groups toxic or lethal to the tumor cells. The general design of such a therapeutic approach depends on the modification of the TSGP antibody and introduction at the new site of an appropriate derivative. Typically, antibodies to TSGP are isolated and purified from the serum of host animals (e.g. rabbits). This may be achieved by a variety of standard procedures including differential precipitation of the $\beta$ and $\gamma$ globulin fraction, gel exlusion chromatography on Sephadex G-150, electrophoretic resolution and lastly, affinity chromatography on a TSGP-Sepharose column. The final step utilizes the specific ligand (TSGP) immobilized by coupling to an inert support (Cuatrecasas et al, cited above) and ensures separation from the bulk of the globulin fraction.

All immunoglobulines are themselves glycoproteins; all contain galactose and most have at least one sialic acid substituent. These loci provide the means of attachment of other functional groups. Typically, the isolated immunoglobulin is either treated with sodium metaperiodate (described earlier) or galactose oxidase [See Gahmberg et al, *J. Biol. Chem.*, 248, 4311 (1973)]. As a result, the carbohydrate moiety of the immunoglobulin is modified and now contains a functional aldehyde grouping, which can be reacted with a variety of agents. Chemicals which may be coupled with the antibody by this procedure include hydrazides and nitrogen mustards. The generalized toxicity of these agents will be strikingly reduced because the cell directed carrier molecule (TSGP-antibody) will permit their introduction to target loci at a small fraction of the concentrations normally employed.

V. DETERMINATION OF TSGP LEVEL IN PATIENT'S SERUM AND UTILIZATION THEREOF AS INDEX OF A THERAPEUTIC REGIMEN:

Since the TSGP is directly related to the presence of cancer, the progress of a given patient undergoing treatment (e.g. chemotherapy, surgery) can be evaluated in part by assaying the levels of TSGP before, during and after therapy. Typically, TSGP levels in serum can be established for a given individual and these monitored. As a rule, patients who undergo surgical removal of tumor are seen for follow-up visits at 3-6 month intervals. Diagnosis of recurrence of the malignancy or efficacy of a drug regimen is generally by non-appearance of symptoms. A routine screen of TSGP levels as part of the regular visit protocol should permit much earlier assessment of tumor reoccurrence of the effectiveness of specific treatment regimens.

What is claimed is:

1. A tumor specific glycoprotein isolated from the perchloric acid soluble fraction of the blood serum of cancer infected humans, said perchloric acid soluble fraction having a sialic acid content above about 0.065 mg per ml of said soluble fraction, said glycoprotein characterized as being soluble in 0.6M perchloric acid at 0° C., having an isoelectric point of from about 4.2 to 4.6 and a molecular weight in the range of 50,000 to 70,000.

2. A tumor specific glycoprotein isolated from the perchloric acid soluble fraction of the blood serum of cancer infected humans, said perchloric acid soluble fraction having a sialic acid content above about 0.065 mg per ml of said soluble fraction, and a protein content above about 0.35 mg per ml of said soluble fraction, said glycoprotein characterized as being soluble in 0.6M perchloric acid at 0° C., having an isoelectric point of from 4.2 to 4.6, and a molecular weight in the range of 50,000 to 70,000.

3. A tumor specific glycoprotein as defined in claim 2 wherein said tumor specific glycoprotein is isolated from the perchloric acid soluble fraction of the blood serum of cancer infected humans, said perchloric acid soluble fraction having a sialic acid content above about 0.080 mg per ml and a protein content above about 0.40 mg per ml.

4. A tumor specific glycoprotein isolatable from blood serum of cancer infected humans, characterized by solubility in 0.6M perchloric acid, a sialic acid content of 30% or more based on the total weight of glucosamine, galactosamine, and sialic acid, a pronase resistant core containing the bulk of the carbohydrate, affinity for wheat germ agglutinin dependent on sialic acid, affinity for diethylaminoethyl Sephadex A-25 and elution with pyridine acetate buffer pH 5.2 at approximately 0.4M concentration, inclusion on Sephadex G-150 in 0.1M pyridine acetate pH 5.2, a molecular weight in the range of 50,000 to 70,000 and an isoelectric point of from about 4.2 to 4.6.

5. A derivative of the tumor specific glycoprotein of claim 4 prepared by reacting said glycoprotein with a periodate.

6. A derivative of the tumor specific glycoprotein of claim 4 containing a reduced sialic acid content prepared by subjecting the sialic acid portion of said glycoprotein to partial removal of hydrolysis of the sialic acid.

7. A method for the detection and diagnosis of cancerous tumors in humans which comprises mixing serum taken from a suspected cancer patient with perchloric acid to precipitate a fraction insoluble therein and subjecting the perchloric acid soluble fraction to gel electrophoresis or isoelectric focusing to detect the presence of a tumor specific glycoprotein as defined in claim 4.

8. A method for detection and diagnosis of cancer which comprises mixing perchloric acid with human sera, analyzing the perchloric acid soluble fraction for N-acetyl neuraminic acid content, and any serum sample found suspect of coming from a cancerous patient by containing an N-acetyl neuraminic acid content in excess of about 0.065 mg per ml of blood serum sample is then verified to eliminate false positives by subjecting a perchloric acid soluble fraction to gel electrophoresis or isoelectric focusing so as to further detect the presence of a tumor specific glycoprotein as defined in claim 4.

9. A method for the radioimmuno assay for the determination of the existence of products of cancerous tumor cell metabolism which comprises isolating a perchloric acid soluble fraction from the serum of the human host, recovering a tumor specific glycoprotein as defined in claim 4 therefrom, utilizing said glycoprotein as an antigen to produce antibody thereto in an animal host, radiolabelling said antibody or said tumor specific glycoprotein or both, and reacting directly or indirectly said labelled product with a perchloric acid soluble fraction of serum from a patient to obtain a glycoprotein antigen-antibody complex, separating said complex and measuring the radioactivity of said complex to determine the presence of and quantity of tumor specific glycoprotein in the serum of the patient.

10. A method of preparing purified tumor specific glycoprotein which comprises mixing blood sera from a tumor containing patient with perchloric acid or trichloroacetic acid, removing the insoluble fraction, neutralizing the said acid soluble fraction, removing the salt formed upon neutralization, dialyzing the soluble portion, concentrating said dialyzed soluble portion, and recovering said tumor specific glycoprotein as defined in claim 4.

11. A method as defined in claim 10 wherein said recovery is by chromatography in a DEAE-Sephadex A-25 column.

12. A method as defined in claim 11 where said glycoprotein is further purified by isoelectric focusing or chromatography on DEAE-Sephadex A-50.

13. A method for the detection and diagnosis of cancer in humans which comprises mixing perchloric acid with human sera to precipitate components insoluble therein and analyzing the perchloric acid soluble fraction for N-acetylneuraminic acid content, and comparing said N-acetyl-neuraminic acid content obtained against a normal standard.

14. A method for the detection and diagnosis of cancer in humans which comprises mixing perchloric acid with human sera to precipitate components insoluble therein, mixing the perchloric acid soluble fraction obtained with a radiolabelled antibody of the tumor specific glycoprotein of claim 4 to obtain a glycoprotein-antibody complex, and measuring the radioactivity of said complex to determine the presence and quantity of tumor specific glycoprotein as defined in claim 4 in the sera.

15. A method for the detection and diagnosis of cancer in humans which comprises mixing perchloric acid with a human sera sample to precipitate components insoluble therein, separating the perchloric acid soluble fraction, admixing said perchloric acid soluble fraction with a measured amount of radiolabelled tumor specific glycoprotein of claim 4 and a measured amount of an antibody of said tumor specific glycoprotein to form an antibody-glycoprotein complex, and measuring the radioactivity of said complex to determine the presence and quantity of tumor specific glycoprotein as defined in claim 4 in the sample.

16. A tumor specific glycoprotein as defined in claim 4 having a radiolabel thereon.

17. A radiolabelled antibody of the tumor specific glycoprotein defined in claim 4.

* * * * *